(12) United States Patent
Gabetta et al.

(10) Patent No.: US 8,318,957 B2
(45) Date of Patent: Nov. 27, 2012

(54) SEMISYNTHESIS PROCESS FOR THE PREPARATION OF 10 DEACETYL-N-DEBENZOYL-PACLITAXEL

(75) Inventors: Bruno Gabetta, Milan (IT); Andrea Gambini, Milan (IT); Ezio Bombardelli, Groppello Cairoli (IT); Gabriele Fontana, Milan (IT)

(73) Assignee: Indena S.p.A., Milan (IT)

( * ) Notice: Subject to any disclaimer, the term of this patent is extended or adjusted under 35 U.S.C. 154(b) by 521 days.

(21) Appl. No.: 12/104,715

(22) Filed: Apr. 17, 2008

(65) Prior Publication Data

US 2008/0200700 A1 Aug. 21, 2008

Related U.S. Application Data

(63) Continuation of application No. 11/244,171, filed on Oct. 6, 2005, now Pat. No. 7,446,126.

(60) Provisional application No. 60/616,840, filed on Oct. 8, 2004.

(30) Foreign Application Priority Data

Oct. 8, 2004 (EP) .................................... 04425752
Apr. 11, 2005 (EP) .................................... 05007888

(51) Int. Cl.
*C07D 305/00* (2006.01)
(52) U.S. Cl. ...................................................... 549/510
(58) Field of Classification Search .................... 549/510
See application file for complete search history.

(56) References Cited

U.S. PATENT DOCUMENTS 6,500,966 B1 12/2002 Bombardelli
6,737,534 B2 5/2004 Pontiroli et al.
6,828,445 B2 12/2004 Pontiroli et al.

FOREIGN PATENT DOCUMENTS

WO 94/07877 4/1994

OTHER PUBLICATIONS

Didier et al, 121:205723 CASREACT (1994).*
Gueritte-Voegelein et:al., "Relationships between the Structure of Taxol Analogues and Their Antimitotic Activity", Journal of Medicinal Chemistry, 1991, vol. 34, No. 3, pp. 992-998.
Dfaz et al., Biochemistry, vol. 32, pp. 2747-2755 (1993).
Tilburg et al., Journal of labeled compounds and radiopharmaceuticals, vol. 47, pp. 763-777 (2004).

* cited by examiner

*Primary Examiner* — Noble Jarrell
*Assistant Examiner* — Raymond Covington
(74) *Attorney, Agent, or Firm* — Young & Thompson

(57) ABSTRACT

A process for the preparation of 10-deacetyl-bis-7,10-trichloroacetylbaccatin III (VI)

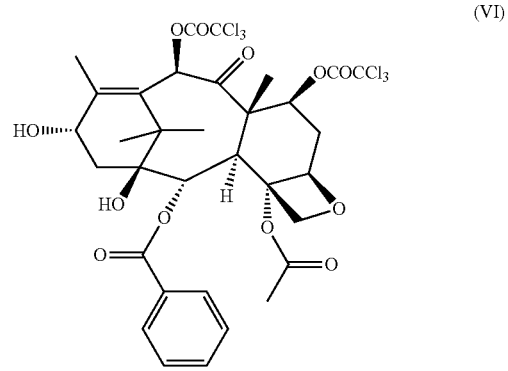

said process comprising:
reacting 10-deacetylbaccatin III with a trichloroacetic acid activated derivative to obtain a reaction mixture, and
performing an isolation step on said reaction mixture obtain purified 10-deacetyl-bis-7,10-trichloroacetyl-baccatin III (VI) having a content, of corresponding 7- or 10 mono-trichloroacetyl derivatives lower than 0.1% as determined by HPLC.

8 Claims, No Drawings

SEMISYNTHESIS PROCESS FOR THE PREPARATION OF 10 DEACETYL-N-DEBENZOYL-PACLITAXEL

This application is a continuation application of Ser. No. 11/244,171, filed Oct. 6, 2005, now allowed, which claims priority to provisional application 60/616,840, filed Oct. 8, 2004, which claims priority to EP 04425752.5, filed Oct. 8, 2004, and EP 05007888.0, filed Apr. 11, 2005. The teachings of the above applications are hereby incorporated by reference.

FIELD OF THE INVENTION

Object of the present invention is a new semisynthesis process for the preparation of 10-deacetyl-N-debenzoyl-paclitaxel (I), a useful synthon for the preparation of taxanes with anti-tumour activity.

The invention also relates to a process for the preparation of 10-deacetyl-bis-7,10-trichloroacetylbaccatin III with a content of the corresponding 7- or 10 mono-trichloroacetyl, derivatives lower than 0.1% as determined by HPLC.

The invention also concerns a process for the preparation of Docetaxel having a purity degree higher than 99%, by subjecting the intermediate (I) obtained by the process of the invention to reaction with di-tert-butyl dicarbonate as well as pharmaceutical compositions comprising said high-purity Docetaxel.

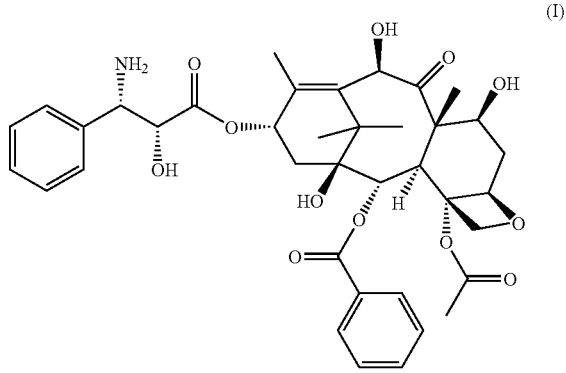

(I)

STATE OF THE ART

A process comprising the esterification with oxazolidines of formula (II)

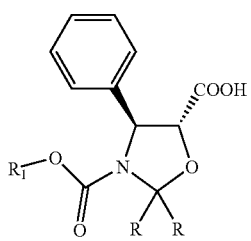

(II)

of 10-deacetylbaccatin protected at the 7- and 10-positions of formula (III)

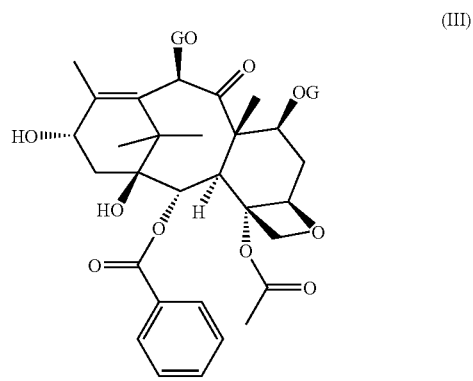

(III)

to give esters of formula (IV)

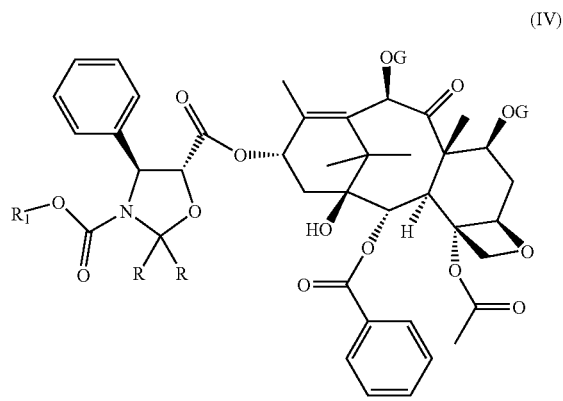

(IV)

has been disclosed in WO 94/07877 for the synthesis of synthon (I), reported in the literature in the early '90s (F. Guéritte-Voegelein et al., J. Med. Chem. 34, 992, 1991).

Liberation of the amino function at the 3'-position and hydroxy groups at the 2'-, 7- and 10-positions from the esters of formula (IV) affords synthon (I).

In particular, according to the above-cited patent application, groups R can be hydrogen, alkyl, alkoxy or variously-substituted phenyl and $R_1$ is alkyl substituted with one or more chlorine atoms. Groups G are alkylsilyl or $R_1$—O—CO— groups wherein $R_1$ is as defined above.

Starting from the intermediates of formula (IV), the hydroxy and the amino functions are liberated by reduction with zinc and acids and, when groups G are alkylsilyl, the hydroxy functions are liberated by acid treatment, for example with hydrofluoric acid.

SUMMARY OF THE INVENTION

The present invention, in a first embodiment thereof, concerns a process for the preparation of 10-deacetyl-N-debenzoyl-paclitaxel (I)

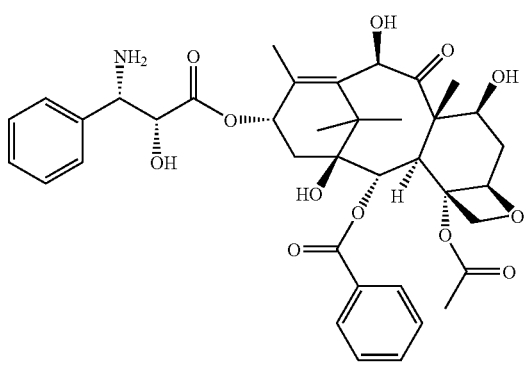

(I)

comprising the following steps:
a) reaction of 2-(2,4-dimethoxyphenyl)-3-(2-nitrobenzene-sulfenyl)-4(S)-phenyl-5(R)-oxazolidinecarboxylic acid (V)

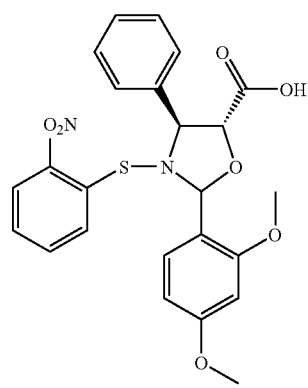

(V)

with 10-deacetyl-bis-7,10-trichloroacetylbaccatin III (VI)

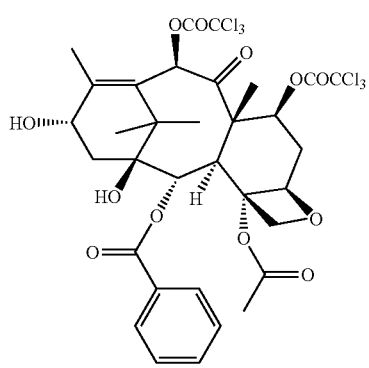

(VI)

to give 2-(2,4-dimethoxyphenyl)-3-(2-nitrobenzensulfenyl)-4(S)-phenyl-5(R)-oxazolidine carboxylic acid, 10-deacetyl-7,10-bis-trichloroaceltybaccatin III 13-yl-ester (VII)

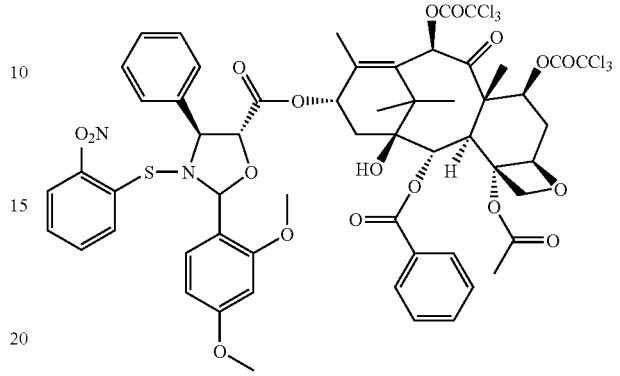

(VII)

b) hydrolysis of the trichloroacetyl groups at the 7- and 10-positions of the compound of formula (VII) to give 2-(2,4-dimethoxyphenyl)-3-(2-nitrobenzensulfenyl)-4(S)-phenyl-5(R)-oxazolidine carboxylic acid, 10-deacetylbaccatin. III 13-yl-ester (VIII)

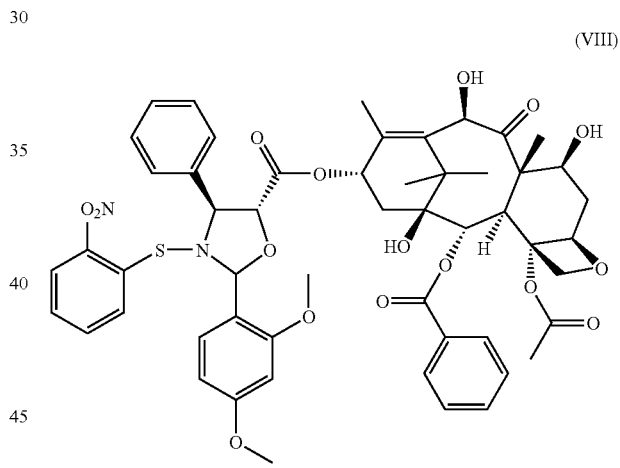

(VIII)

c) acid treatment of the compound formula (VIII) to give 10-deacetyl-N-debenzoyl-paclitaxel (I).

The invention also provides as novel intermediates 2-(2,4-Dimethoxyphenyl)-3-(2-nitrobenzensulfenyl)-4(S)-phenyl-5(R)-oxazolidine carboxylic acid, 10-deacetyl-7,10-bis-trichloroacetylbaccatin III 13-yl-ester (VII) and 2-(2,4-Dimethoxyphenyl)-3-(2-nitrobenzensulfenyl)-4(S)-phenyl-5(R)-oxazolidine carboxylic acid, 10-deacetylbaccatin III 13-yl-ester (VIII).

The invention also concerns a process for the preparation of 10-deacetyl-bis-7,10-trichloroacetylbaccatin III with a content of the corresponding 7- or 10 mono-trichloroacetyl derivatives lower than 0.1% as determined by HPLC, comprising the silica gel chromatography of the reaction mixture.

A further object if the invention is provided by Docetaxel having a purity degree higher than 99% as well as pharmaceutical compositions comprising it.

DESCRIPTION OF THE INVENTION

The present invention relates to a process for the synthesis of synthon (I)

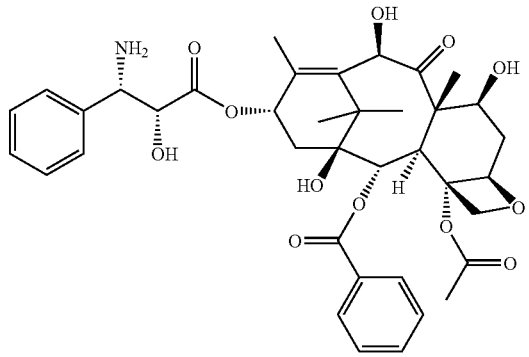

(I)

in high yield and/or quality. The process moreover does not require the polluting or difficult to handle reagents, such as zinc and hydrofluoric acid.

The process consists in the reaction of 2-(2,4-dimethoxyphenyl)-3-(2-nitrobenzenesulfenyl)-4(S)-phenyl-5(R)-oxazolidinecarboxylic acid (V)

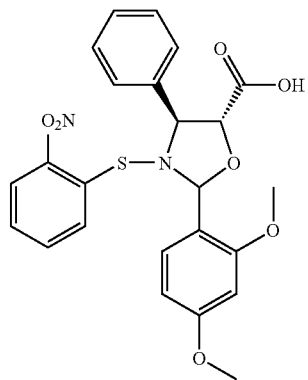

(V)

with 10-deacetyl-bis-7,10-trichloroacetylbaccatin III (VI)

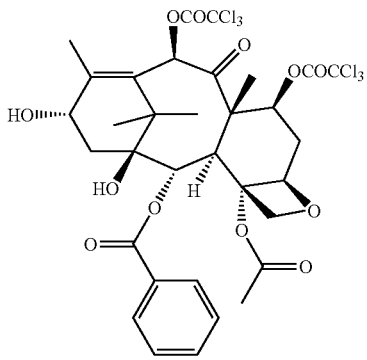

(VI)

to give the ester (VII)

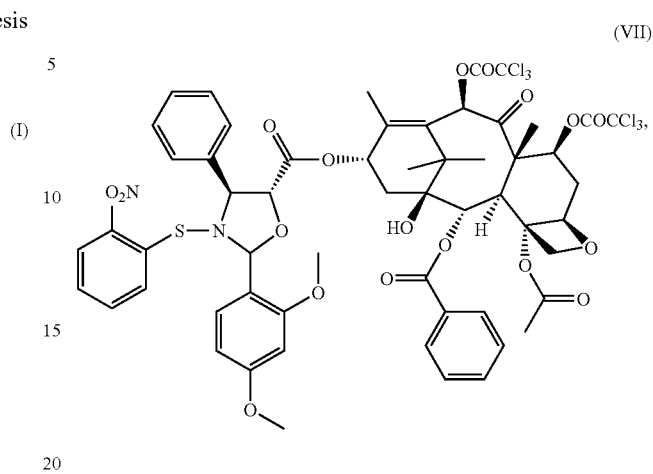

(VII)

wherefrom synthon (I) is obtained after liberation of the amino and hydroxy functions.

The compound of formula (VII) is novel and is a further object of the present invention.

The oxazolidine acid (V) either 2R, 2S or a mixture thereof, is equally useful in the synthesis, since the chiral center at the 2-position of the oxazoline ring is removed from intermediate (VII) upon liberation of the hydroxy and amino functions. In other words, the relative ratio between the diastereoisomers does not impair the performance of the synthesis.

The oxazolidine acid (V) is easily prepared by acid treatment of the corresponding alkali salts, whose preparation has been disclosed in WO 03/087077 A1.

Compared to other oxazolidine acids, acid (V) is characterised by remarkable stability which allows to easily carry out the esterification with synthon (VI).

Moreover, after the esterification, the liberation of the amino and hydroxy functions contained in the acid residue can be easily carried out by treatment with acids, without the need to adopt drastic conditions.

The taxane synthon (VI) can be obtained from the natural metabolite 10-deacetylbaccatin III through esterification of the 7- and 10-positions by treatment with trichloroacetic acid activated derivatives, according to known esterification methods. Preferably, synthon (VI) is obtained by reaction with trichloroacetic acid chloride at a temperature around 0° C., using pyridine as the solvent. Preferably, 10-deacetyl-bis-7,10-trichloroacetylbaccatin III (VI), is purified from its corresponding 7- and 10-mono-trichloacetyl esters by silica gel chromatography or equivalent methods. The residual amount of said impurities should not exceed 0.1% as measured by HPLC % peaks.

According to the present invention, the esterification of (VI) with the oxazolidine acid (V) to give (VII) can be carried out in the presence of a condensing agent, such as a diimide, for example dicyclohexylcarbodiimide, and an activating agent, for example 4-dimethylamino-pyridine or 4-pyrrolidino-pyridine in a solvent selected from an ether, such as ethyl ether, diisopropyl, ether, tetrahydrofurane or dioxane; an ester, such as ethyl, propyl or butyl acetate; an aromatic hydrocarbon, such as benzene, toluene or o-, m-, p-xylene; or a halogenated aliphatic hydrocarbon, for example methylene chloride, chloroform or dichloroethane. Carrying out the esterification in methylene chloride at the temperature of about 20° C. is particularly advantageous.

The preparation of synthon (I) from ester (VII) requires removal of the trichloroacetyl groups from the 7- and 10-positions and liberation of the amino and hydroxy functions from the oxazolidine residue.

As mentioned above, the amino and hydroxy functions can be, easily liberated from the oxazolidine residue by acid treatment. On the contrary, the hydrolysis of the trichloroacetic esters can be conveniently carried out by mild alkaline treatment, preferably by reaction with ammonium hydroxide.

It has been observed that, if the liberation of the amino and hydroxy functions from the oxazolidine residue is carried out first, massive migration of a trichloroacetyl group from the baccatin residue to the free amino function occurs, with consequent formation of a trichloroacetamido function, which could be transformed in an amino function only under conditions that would be detrimental to the structure of the baccatin skeleton. As a consequence, the preparation of synthon (I) requires first the removal of the trichloroacetic groups at the 7- and 10-positions of (VII) to give ester (VIII).

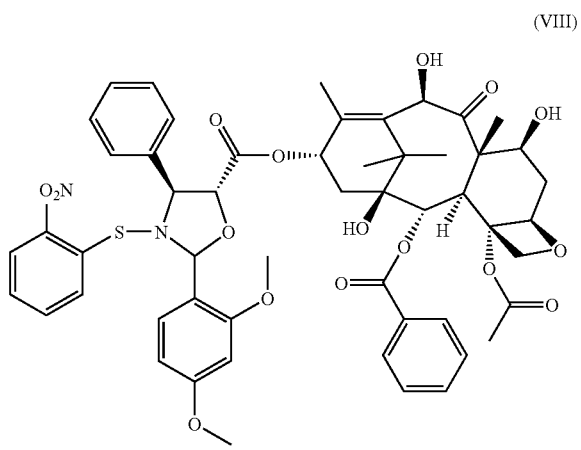

(VIII)

Also the compound of formula (VIII) is novel and is a further object of the present invention. Preferably, the removal of the trichloroacetic groups is carried out at room temperature by treatment with ammonium hydroxide in tetrahydrofuran as the solvent.

The liberation of the amino and hydroxy functions is carried out by treatment with acids, preferably with aqueous hydrochloric acid, in alcoholic solution, for example in methanol at a temperature of about 20° C. After dilution with water and removal of reaction by-products with organic solvents, such as aliphatic hydrocarbons and halogenated haliphatic hydrocarbons, for example n-hexane and methylene chloride, synthon (I) is isolated by alkalinization of the aqueous phase, extraction in an organic solvent, for example methylene chloride or ethyl acetate, concentration and precipitation in an aliphatic hydrocarbon, such as n-hexane. The process of the invention provides synthon (I) with purity higher than 98%, without chromatographic purifications.

Docetaxel, can be advantageously obtained from said intermediate with a purity degree higher than 99%, preferably higher than 99.4%, by reaction with di-tert-butyl dicarbonate.

The reaction is preferably carried out in solvents such as alcohols, (methanol, ethanol, isopropanol, preferably ethanol), chlorinated hydrocarbons (methylene chloride, chloroform, preferably methylene chloride) or mixtures thereof, in the absence of bases.

The process is advantageous since Docetaxel may be obtained in high purity without cumbersome chromatographic purifications, by crystallizations from suitable solvents, preferably from ethanol/water and/or acetone/hydrocarbon mixtures. Docetaxel obtained using the process subject of the present invention is characterized by a purity degree higher than 99% (HPLC area %) and content of 7-epi docetaxel and 10-dehydrodocetaxel lower than 0.1% each (HPLC area %).

The invention will be now illustrated in more detail in the following examples.

EXAMPLES

Example 1

10-Deacetyl-7,10-bistrichloroacetylbaccatin III (VI)

10-Deacetylbaccatin III (15 g) is treated with 6.6 ml of trichloroacetyl chloride in 60 ml of pyridine at 0-5° C. for 1 hour under stirring. The mixture is diluted with 100 ml of methylene chloride and 100 ml of 4 N hydrochloric acid. The phases are separated and the organic one is washed with 100 ml of 4 N hydrochloric acid and 50 ml of water saturated with sodium chloride. The organic phase is concentrated under vacuum and the residue is taken up with 100 ml of toluene. Product (VI) is collected by filtration and, dried under vacuum at 5.0° C. The latter is dissolved at 35° C. in $CH_2Cl_2$ (80 ml) and purified by column chromatography using 800 g of Kiesegel 60 Merck (eluent: $CH_2Cl_2$). The fractions are combined (TLC: $CH_2Cl_2$) and checked by HPLC. The total content of mono 7 and 10-trichloroacetyl baccatin III must be less than 0.1%. Purified compound (VI) is precipitated in toluene to yield (17.8 g, 21.4 mmol, 660/26/B, A % purity: 99%, yields: 78%)

Example 2

2-(2,4-Dimethoxyphenyl)-3-(2-nitrobenzensulfenyl)-4(S)-phenyl-5(R)-oxazolidine carboxylic acid, 10-deacetyl-7,10-bis-trichloroacetylbaccatin III 13-yl-ester (VII)

A solution containing 10.3 g of (V) in the form of sodium salt in 100 ml of water is cooled to 0-5° C. and adjusted to pH 2-3 with a 2 M sodium bisulfate solution. The reaction mixture is stirred at 0° C. for 15 minutes and then $CH_2Cl_2$ (70 ml) is added. The two phases are separated and the aqueous layer extracted once with $CH_2Cl_2$ (1×50 ml). The combined organic phases are washed with a saturated solution of NaCl (1×25 ml) (360 g/l) and dried over anhydrous $Mg_2SO_4$ (3 g, KF 0.12%). After filtration, the solution is concentrated under vacuum at room temperature until 100 mL. To the yellow solution 12 g of (VI) are added, followed by 0.175 g (1.42 mmol) of dimethylaminopyridine (DMAP) and, after complete dissolution of the reagent, 5.88 g of dicyclohexylcarbodiimide (DCC). The reaction mixture is stirred at room temperature for an hour. No starting (VI) is detected by TLC (ethyl acetate/hexane:1/2, detection by spraying with a solution containing $H_2SO_4$ (31 mL), ammonium molybdate (19 g) and $(NH_4)_4Ce(SO_4)_4 \cdot 2 H_2O$ (1.9 g) in water (500 mL) and heating at 130° C. for 5 min). The precipitate of dicyclohexylurea (DCU) formed is filtered off and washed with $CH_2Cl_2$ (1×20 mL). The chloromethylene solution is evaporated to dryness yielding 24 g of (VII).

Example 3

2-(2,4-Dimethoxyphenyl)-3-(2-nitrobenzensulfenyl)-4(S)-phenyl-5(R)-oxazolidine carboxylic acid, 10-deacetylbaccatin III 13-yl-ester (VIII)

A solution containing 24 g of (VII) in 100 ml of tetrahydrofuran is concentrated under vacuum, the residue, taken up with 150 ml of tetrahydrofurane (THF) and the mixture concentrated under vacuum till 100 ml.

Conc ammonium hydroxide 33% ($NH_4OH$, 1.8 ml, 30 mmol) is added at room temperature in 5 minutes and the reaction mixture is stirred at room temperature for two hours. TLC of the mixture shows no compound (VII) (ethyl acetate/hexane:4/3). The solution is concentrated under vacuum and the residue taken up with MeOH (125 ml). The suspension is stirred for 2 hours. The precipitate is filtered through a sintered glass filter and washed with (10 ml) of MeOH to get compound (VIII) (13 g, 12 mmol, HPLC A %=93%, yield 84%). The mother liquor contains 9.3 g of residue to be discarded.

Example 4

10-Deacetyl-N-debenzoyl-paclitaxel (I)

A suspension of 13 g of (VIII) in 260 ml of methanol is treated for 30 minutes at room temperature under stirring with 4.2 ml of concentrated aqueous hydrochloric acid diluted with 130 ml methanol. The reaction mixture is stirred at room temperature for four hours and the suspension becomes a clear yellow solution. TLC of the mixture shows no compound (VIII) (ethyl acetate/hexane:4/3). The solution is slowly diluted with water (350 ml) (to avoid the formation of precipitate) and the homogeneous solution is stirred at room temperature for 30 minutes. $CH_2Cl_2$ (200 ml) is added, the two phases are separated and the aqueous layer extracted again with $CH_2Cl_2$ (2×100 ml). The organic phases are eliminated. The hydro-alcoholic phase is cooled down to 0-5° C. and diluted with $CH_2Cl_2$ (1×100 ml). Under vigorous stirring at 0-5° C. conc. ammonia (3.1 ml, $NH_4OH$) is added dropwise (a 1 degree increase of the temperature is obtained) up to pH=7-8. The biphasic reaction is stirred at the same temperature for 20 minutes, then the phases are separated and the aqueous layer is extracted with $CH_2Cl_2$ (5×100 ml).

The combined organic layers are concentrated under vacuum till 100 ml and at room temperature under stirring the product crystallizes. The precipitate is filtered through a glass sintered filter and after drying under vacuum at 40° C. overnight, 7.5 of the title compound are obtained.

Example 5

Preparation of Docetaxel

Compound (I) (16 g, HPLC purity assay: 90.57%, 20.49 mmol) is dissolved in a mixture 1:1 of absolute EtOH and $CH_2Cl_2$ (320 ml) and to the slightly yellowish solution di-tert-butyl dicarbonate $(BOC)_2O$ in, $CH_2Cl_2$ (24.18 mmol, 5.27 g dissolved in 5 ml of $CH_2Cl_2$) is added. At the end of the addition the reaction mixture is stirred for 16 hours at room temperature. TLC shows no compound (I) ($CH_2Cl_2$/MeOH: 9/1, detection by spraying with a solution containing $H_2SO_4$ (31 ml), ammonium molybdate (19 g) and $(NH_4)_4Ce(SO_4)_4 \cdot 2 H_2O$ (1.9 g) in water (500 ml) and heating at 130° C. for 5 min). The $CH_2Cl_2$ is distilled off and acetic acid is added (0.39 ml) to the solution. The acidic ethanol solution is heated at 50° C. and pure water (320 ml) is added dropwise. The mixture is left at 50° C. for an hour and at room temperature for additional 2 hours. The precipitate is filtered through a glass sintered filter and transferred within a vacuum oven and maintained under vacuum at 40° C. overnight to yield 16.75 g of semi-purified Docetaxel and 1 g of mother liquor that can be eliminated.

The crude product is crystallized twice: semi-purified Docetaxel is dissolved at 50° C. in 95% ethanol (160 ml) and acetic acid (0.39 ml) is added. The mixture, after the addition of pure water (320 ml), is left at 50° C. for an hour and at room temperature for additional 2 hours. The precipitate is filtered through a glass sintered filter and transferred within a vacuum oven and maintained under vacuum at 40° C. overnight to get 15.25 g of Docetaxel and 0.4 g of mother liquor that can be eliminated. The second crystallization is performed re-dissolving the product at 30° C. in acetone (150 ml) and adding heptane (150 ml). The mixture is left at room temperature for three hours. The precipitate is filtered through a glass sintered filter and transferred within a vacuum oven and maintained under vacuum at 40° C. overnight to get 13.9 g of Docetaxel (HPLC purity higher than 99.4%, <0.1% of 7-epi docetaxel and <0.1% 10-dehydrodocetaxel).

The invention claimed is:

1. A process for the preparation of 10-deacetyl-bis-7,10-trichloroacetylbaccatin III (VI)

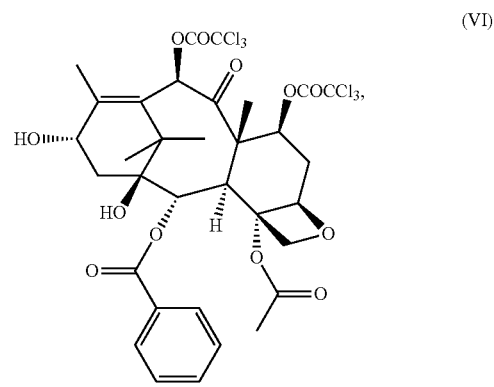

said process comprising:
reacting 10-deacetylbaccatin III with a trichloroacetic acid activated compound to obtain a reaction mixture, and
performing an isolation step on said reaction mixture using silica gel chromatography to obtain purified 10-deacetyl-bis-7,10-trichloroacetylbaccatin III (VI) having a content of corresponding 7- or 10 mono-trichloroacetyl compounds lower than 0.1% as determined by HPLC.

2. A process for the preparation of Docetaxel said process comprising:
a) reacting 10-deacetylbaccatin III with a trichloroacetic acid activated compound to obtain a reaction mixture, and
performing an isolation step on said reaction mixture using silica gel chromatography to obtain purified 10-deacetyl-bis-7,10-trichloroacetylbaccatin III (VI)

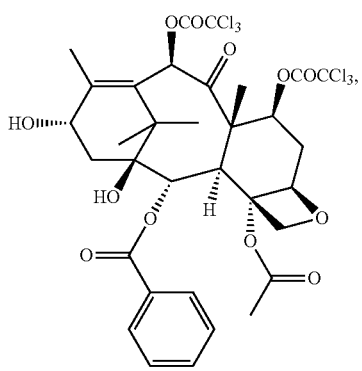

(VI)

said 10-deacetyl-bis-7,10-trichloroacetylbaccatin III (VI) having a content of corresponding 7- or 10 mono-trichloroacetyl compounds lower than 0.1% as determined by HPLC;

b) reacting 2-(2,4-dimethoxyphenyl)-3-(2-nitrobenzenesulfenyl)-4(S)-phenyl-5(R)-oxazolidine carboxylic acid (V)

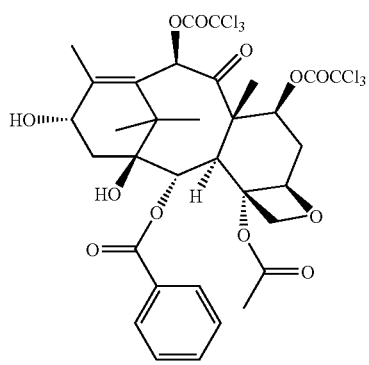

(VI)

with 10-deacetyl-bis-7,10-trichloroacetylbaccatin III (VI) to give 2-(2,4-dimethoxyphenyl)-3-(2-nitrobenzensulfenyl)-4(S)-phenyl-5(R)-oxazolidine carboxylic acid, 10-deacetyl-7,10-bis-trichloroacetylbaccatin III 13-yl-ester (VII)

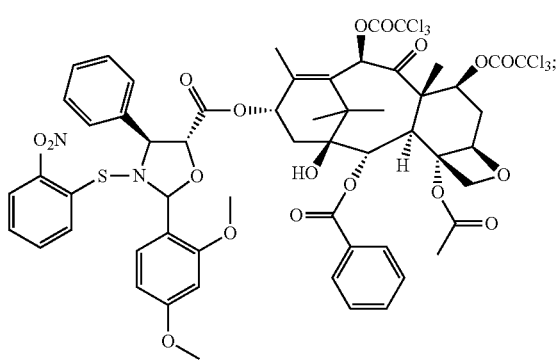

(VII)

c) hydrolyzing the trichloroacetyl groups at the 7- and 10-positions of 10-deacetyl-7,10-bis-trichloroacetyl-baccatin III 13-yl-ester (VII) to give 2-(2,4-dimethoxyphenyl)-3-(2-nitrobenzensulfenyl)-4(S)-phenyl-5(R)-oxazolidine carboxylic acid, 10-deacetylbaccatin III 13-yl-ester (VIII)

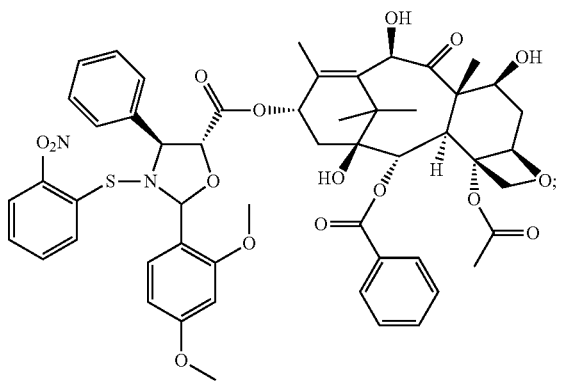

(VIII)

d) treating the 2-(2,4-dimethoxyphenyl)-3-(2-nitrobenzensulfenyl)-4(S)-phenyl-5(R)-oxazolidine carboxylic acid, 10-deacetylbaccatin III 13-yl-ester (VIII) with acid to give 10-deacetyl-N-debenzoyl-paclitaxel (I)

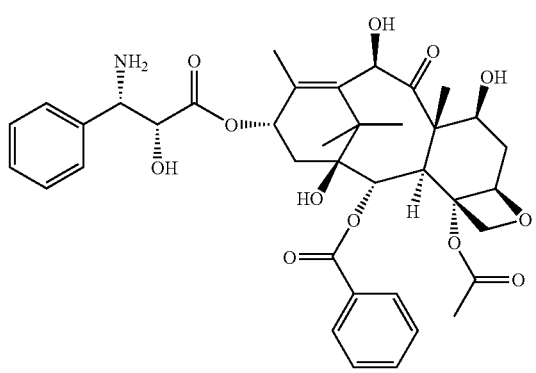

(I)

e) reacting 10-deacetyl-N-debenzoyl-paclitaxel (I) with di-tert-butyl dicarbonate to obtain a reaction mixture, and performing an isolation step using silica gel chromatography and at least one crystallization step using ethanol/water and/or acetone/hydrocarbon mixtures on said reaction mixture to obtain purified Docetaxel.

3. The process according to claim 2 wherein the reaction step is carried out in solvents selected from alcohols, chlorinated hydrocarbons or mixtures thereof, in the absence of bases.

4. The process according to claim 2, resulting in purified Docetaxel having a purity degree higher than 99% obtained without chromatographic purification and with a content of corresponding 7-epi or 10-dehydro compounds lower than 0.1% each.

5. Docetaxel having a purity degree higher than 99% and with a content of corresponding 7-epi or 10-dehydro compounds lower than 0.1% each.

6. A pharmaceutical composition comprising Docetaxel of claim 5.

7. The process according to claim 1, wherein said trichloroacetic acid activated compound is trichloroacetyl chloride.

8. The process according to claim 1, wherein said reaction step is carried out at a temperature of 0° C. using pyridine as a solvent.

* * * * *